(12) United States Patent
Homan et al.

(10) Patent No.: US 11,033,188 B2
(45) Date of Patent: Jun. 15, 2021

(54) IMAGING DEVICE AND METHOD FOR GENERATING AN IMAGE OF A PATIENT

(71) Applicant: KONINKLIJKE PHILIPS N.V., Eindhoven (NL)

(72) Inventors: Robert Johannes Frederik Homan, Batenburg (NL); Bernardus Hendrikus Wilhelmus Hendriks, Eindhoven (NL); Drazenko Babic, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 504 days.

(21) Appl. No.: 15/531,019

(22) PCT Filed: Nov. 26, 2015

(86) PCT No.: PCT/EP2015/077707
§ 371 (c)(1),
(2) Date: May 26, 2017

(87) PCT Pub. No.: WO2016/083483
PCT Pub. Date: Jun. 2, 2016

(65) Prior Publication Data
US 2017/0319075 A1 Nov. 9, 2017

(30) Foreign Application Priority Data
Nov. 27, 2014 (EP) .................................. 14195180

(51) Int. Cl.
*A61B 8/00* (2006.01)
*A61B 5/00* (2006.01)
(Continued)

(52) U.S. Cl.
CPC .......... *A61B 5/0077* (2013.01); *A61B 5/0035* (2013.01); *A61B 5/1128* (2013.01);
(Continued)

(58) Field of Classification Search
CPC ... A61B 5/0077; A61B 6/5235; A61B 5/0035; A61B 5/1128; A61B 6/5247; A61B 6/4441
See application file for complete search history.

(56) References Cited

U.S. PATENT DOCUMENTS 8,494,227 B2  7/2013  Prokoski
8,553,839 B2  10/2013  Hendriks
(Continued)

FOREIGN PATENT DOCUMENTS

JP  2006102360 A  4/2006
JP  2012107942 A  6/2012
(Continued)

OTHER PUBLICATIONS

Juan, L. et al "A Comparison of SIFT, PCA-SIFT and SURF", International Journal of Image Processing (IJIP). vol. 3, No. 4, pp. 143-152, 2009.
(Continued)

*Primary Examiner* — Joel Lamprecht (57) ABSTRACT

The present invention relates to an imaging device (100) for generating an image of a patient (P), the imaging system (100) comprising: a camera arrangement (10), which is configured to provide a first image information (I1) of the patient (P) using a first wavelength band, and which is configured to provide a second image information (I2) of the patient (P) using a second wavelength band. The first wavelength band and the second set of wavelength band are different; and the first and/or second image information comprises landmark information of landmarks (M) of a patient (P). The landmark information is derived by at least one wavelength band outside the visible spectrum. Further, a data processor (30) is provided, which is configured to generate a fused image (IE) based on the first image infor-
(Continued)

mation (I1) and the second image information (I2), and which is configured to detect the landmarks (M) in the fused image (IE).

18 Claims, 6 Drawing Sheets

(51) Int. Cl.
*A61B 6/00* (2006.01)
*A61B 5/11* (2006.01)

(52) U.S. Cl.
CPC .......... *A61B 6/4441* (2013.01); *A61B 6/5235* (2013.01); *A61B 6/5247* (2013.01)

(56) References Cited

U.S. PATENT DOCUMENTS

| | | | |
|---|---|---|---|
| 2003/0108223 A1 | 6/2003 | Toyama | |
| 2006/0062448 A1 | 3/2006 | Hirsch | |
| 2007/0158569 A1 | 7/2007 | Zeman | |
| 2007/0249913 A1 | 10/2007 | Freeman | |
| 2011/0152692 A1* | 6/2011 | Nie | A61B 5/0071 600/473 |
| 2011/0196240 A1 | 8/2011 | Mitani | |
| 2012/0071765 A1 | 3/2012 | Chinnock | |
| 2013/0114868 A1 | 5/2013 | Burlina | |
| 2013/0137961 A1 | 5/2013 | Barnes | |
| 2013/0194261 A1 | 8/2013 | Cummins | |
| 2013/0302746 A1 | 11/2013 | Liang | |
| 2014/0031668 A1 | 1/2014 | Mobasser | |
| 2014/0161307 A1 | 6/2014 | Yi | |

FOREIGN PATENT DOCUMENTS

| | | |
|---|---|---|
| JP | 2013244343 A | 12/2013 |
| WO | 200129769 A2 | 4/2001 |
| WO | 2008130903 A1 | 10/2008 |
| WO | 2010067281 A1 | 6/2010 |
| WO | 2010131180 A1 | 11/2010 |
| WO | 2014013393 A2 | 1/2014 |

OTHER PUBLICATIONS

Lindstrom, P. "Triangulation made easy", Proc. IEEE Conf. Comput. Vis. Patt. Recog., Jun. 2010.
Horn, B.K.P. "Closed-form Solution of Absolute Orientation using Unit Quaternions," Journal of the Optical Society A, vol. 4, 629-642 (Apr. 1987).
Wang, F. et al "High-contrast subcuatenous vein detection and localization using multispectral imaging", Journal of Biomedical Optics vol. 18 (2013) 050504-1.
Paquit, Vincent C. et al "3D and Multispectral Imaging for Subcutaneous Veins Detection", 2009 Optical Society of America.

* cited by examiner

IMAGING DEVICE AND METHOD FOR GENERATING AN IMAGE OF A PATIENT

CROSS-REFERENCE TO PRIOR APPLICATIONS

This application is the U.S. National Phase application under 35 U.S.C. § 371 of International Application No. PCT/EP2015/077707, filed on Nov. 26, 2015, which claims the benefit of European Patent Application No. 14195180.6, filed on Nov. 27, 2014. These applications are hereby incorporated by reference herein.

FIELD OF THE INVENTION

The present invention relates to image processing using medical imaging of a patient using and processing information about landmarks. In particular, the present invention relates to an imaging device and a method for generating an image of a patient.

BACKGROUND OF THE INVENTION

Image guided minimal invasive therapy is gaining its momentum in multitude of interventional and minimal invasive therapies. The main premises of this approach are: less trauma to the patient, quick recovery time, less blood loss and improved clinical outcome. To provide for enhanced image guidance while performing the minimal invasive interventional therapies, imaging and navigation have to be seamlessly combined and integrated hardware- and software-wise.

SUMMARY OF THE INVENTION

There may be a need to improve imaging arrangements and methods for imaging and tracking a patient.

These needs are met by the subject-matter of the independent claims. Further exemplary embodiments are evident from the dependent claims and the following description.

A first aspect of the present invention relates to an imaging device for generating an image of a patient. The imaging device comprises a camera arrangement, which is configured to provide a first image information of the patient using a first wavelength band, and which is configured to provide a second image information of the patient using a second wavelength band, wherein the first wavelength band and the second wavelength band are different. The first and/or second image information comprises landmark information of blood vessels or other superficial tissue structures in the skin of a patient as natural markers. Further, the device comprises a data processor, which is configured to generate a fused image showing the natural markers in a contrast above a predefined threshold value based on the first image information and the second image information. The data processor is further configured to detect the natural markers in the fused image.

In an example, the data processor is configured to optically resolve landmarks in the fused image.

The present invention advantageously allows spectrally resolving natural position markers by a camera arrangement, which markers are for instance present on the skin of the patient, but which may be not visible, i.e. spectrally resolvable, by a RGB camera.

For example, an improved imaging device may be provided, which allows enhanced patient tracking, preferably without using artificial markers, i.e. using already present but poorly visible natural position markers or landmarks.

For example, a medical imaging system is provided, which may be used for interventional procedures, and which uses cameras integrated in detector housing for enhanced image guidance.

The present invention is based on the idea that markers are primarily required due to insufficient contrast resolution of skin tissue as well as missing of distinct anatomical markers on the patient surface, i.e. the skin, itself. On the other hand, blood vessels or other superficial tissue structures in the skin could be good candidates for natural anatomical markers, but blood vessels or other superficial tissue structure in the skin are not well visible using normal optical cameras using the visible light spectrum.

The imaging device/imaging system as well as the method according to the present invention provides the option to use blood vessels or other superficial tissue structures as natural markers by combining image data from different wavelength bands. In an example, the first and second wavelength bands are selected so as to provide a relatively high contrast for the natural markers in the fused image. Preferably, the wavelength bands contain one band in the visible range and one band in the invisible range, for instance infrared or ultraviolet. A fused image may be created from the two images from each band, which shows the blood vessels or other superficial tissue structure in the skin in high contrast. The image fusion preferably includes a partial subtraction or a further data operation.

For example, from the high—high in terms of above a contrast threshold value—contrast vessel images, i.e. two images from different view positions, feature points are detected, from which a three-dimensional model of an anatomical tissue structure or even the whole patient is created. Displacements of tissue structures within the three-dimensional model can be accurately tracked by the present invention and a time-depending model may accurately represent any displacement of the patient itself.

The present invention advantageously allows obtaining a high contrast image of the blood vessels by an image of the skin, which is recorded in at least two wavelength bands, creating a fused image from the two recorded images in a way that may include the step of partially subtract the first image from the second image. The subtraction may be performed in real time.

According to a further, second aspect of the present invention, a medical imaging system comprises an imaging device according to the first aspect or any implementation form of the first aspect as provided. The medical imaging system further comprises a display device for displaying the fused image, and an X-ray device for providing X-ray image information of the patient. The data processor is configured to generate the fused image based on the first image information and the second image information and the X-ray image information.

According to a further, third aspect of the present invention, a method for generating an image of a patient is provided. The method comprises the following steps of:
a) providing a first image information of the patient using a first wavelength band by a camera arrangement;
b) providing a second image information of the patient using a second wavelength band by the camera arrangement; wherein the first wavelength band and the second wavelength band are different; and wherein the first and/or second image information comprises landmark information of blood vessels or other superficial tissue structures in the skin of a patient (P) as natural markers (M); and c) generating a fused image showing the natural markers in a contrast above a predefined threshold value based on the first image information and the second image information by a data processor and detecting the natural markers in the fused image.

Advantages and embodiments of the present invention are represented by the dependent claims of the present invention as presented in the following.

According to an exemplary embodiment of the present invention, the camera arrangement is configured to record the first image information in a first position with respect to the patient, and to record the second image information in a second position with respect to the patient. This advantageously allows an improved triangulation and consequently an improved three-dimensional modeling or patient tracking. The image information from two different positions advantageously enables the determination of depth and three-dimensional (3D) structures obtained on the basis of the image information and the landmarks identified therein.

According to a further exemplary embodiment of the present invention, the camera arrangement comprises a camera device, which is configured to provide both the first image information and the second image information. This advantageously allows an improved imaging and optically resolving of natural landmarks as, for instance, blood vessels underneath the skin. The camera device may also be referred to as a primary camera or integrated camera or dual-image camera.

According to a further exemplary embodiment of the present invention, the camera device is configured to be moved along a predefined trajectory comprising the first position and the second position. This advantageously allows providing information of triangulation or three-dimensional modeling of displacements of tissue structures within a three-dimensional space using a single camera device According to a further exemplary embodiment of the present invention, the camera device is configured to provide the first image information of the patient using a wavelength band within an infrared spectrum as the first wavelength band. This advantageously allows an improved spectrally resolving of natural position markers.

According to a further exemplary embodiment of the present invention, the camera arrangement comprises a first camera device, which is configured to provide the first image information, and a second camera device, which is configured to provide the second image information; the first camera device is configured to record the first image information in the first position, and the second camera device is configured to record the second image information in the second position. This advantageously allows building up an improved three-dimensional model of the patient or a three-dimensional model of structures of the patient.

According to a further exemplary embodiment of the present invention, the first camera device is configured to provide the first image information of the patient using a wavelength band within an infrared spectrum as the first wavelength band. This advantageously allows an improved spectrally resolving of the landmarks.

According to a further exemplary embodiment of the present invention, the second camera device is configured to provide the second image information of the patient using a wavelength band within an infrared spectrum as the second wavelength band. This provides an improved detection of the landmarks.

According to a further exemplary embodiment of the present invention, the data processor is configured to generate a three-dimensional model of structures identified by optically resolving the landmarks.

According to a further exemplary embodiment of the present invention, the imaging device may comprise a display device for displaying the fused image. This improves the data communication of the results of data processing carried out by the image information processing.

According to a further exemplary embodiment of the present invention, the imaging device is configured to detect a motion of the patient based on a continuous recording by the camera arrangement and a continuous generating of the fused image by the data processor, resulting in a fused video data steam. This advantageously allows an improved patient tracking, i.e. a tracking of any movements of a patient.

A computer program performing the method of the present invention may be stored on a computer-readable medium. A computer-readable medium may be a floppy disk, a hard disk, a CD, a DVD, an USB (Universal Serial Bus) storage device, a RAM (Random Access Memory), a ROM (Read Only Memory) and an EPROM (Erasable Programmable Read Only Memory). A computer-readable medium may also be a data communication network, for example the Internet, which allows downloading a program code.

The methods, systems and devices described herein may be implemented as software in a Digital Signal Processor, DSP, in a micro-controller or in any other side-processor or as hardware circuit of a medical device within an application specific integrated circuit, ASIC.

The present invention can be implemented in digital electronic circuitry, or in computer hardware, firmware, software, or in combinations thereof, e.g. in available hardware of a medical imaging device or in a new hardware dedicated for processing the methods described herein.

These and other aspects of the present invention will become apparent from and be elucidated with reference to the embodiments described hereinafter.

BRIEF DESCRIPTION OF THE DRAWINGS

A more complete appreciation of the present invention and the advantages thereof will be more clearly understood by reference to the following schematic drawings, which are not to scale, wherein.

DETAILED DESCRIPTION OF EMBODIMENTS

The illustration in the drawings is purely schematic and does not intend to provide scaling relations or size information. In different drawings or figures, similar or identical elements are provided with the same reference numerals. Generally, identical parts, units, entities or steps are provided with the same reference symbols in the description.

Figure 1:
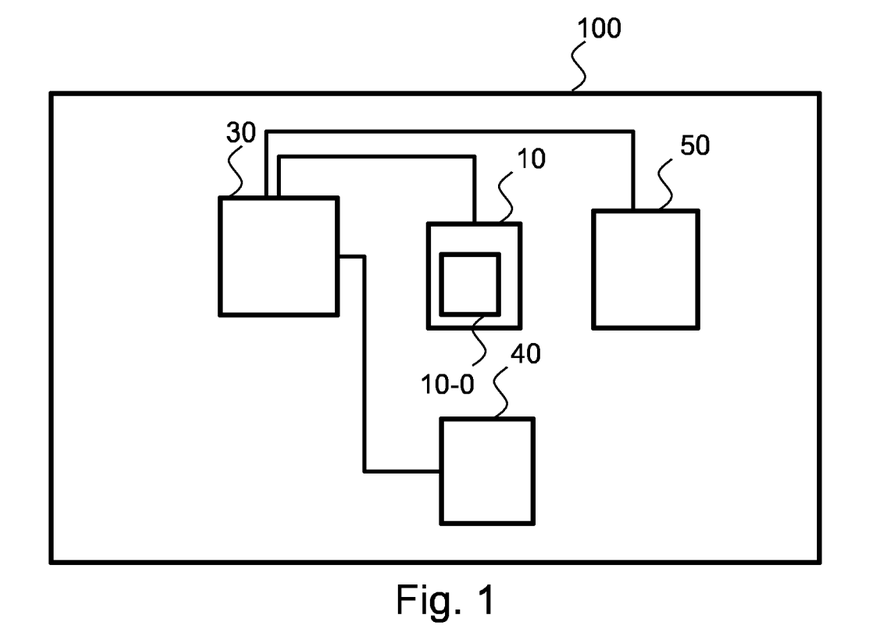
FIG. 1 shows a schematic diagram of an imaging device for generating an image of a patient according to an exemplary embodiment of the present invention.

FIG. 1 shows an imaging device 100 for generating an image of a patient according to an exemplary embodiment of the present invention. FIG. 1 shows the imaging device 100 comprising a camera arrangement 10, and a data processor 30.

The imaging device 100 may further comprise an X-ray device 40 for providing an X-ray image $I_3$ of a patient P. The imaging system 100 may further comprise a display device 50 for displaying a fused image IE.

The camera arrangement 10 may be configured to provide a first image information $I_1$ of the patient P using a first wavelength band, and to provide a second image information $I_2$ of the patient P using a second wavelength band. The first wavelength band and the second set of wavelength band are different, and the first and/or second image information comprises landmark information of landmarks M of a patient P. In particular, at least one wavelength band may be outside the visible spectrum, and more specifically within the infrared spectrum.

According to an exemplary embodiment of the present invention, the camera arrangement 10 may comprise one camera device 10-0, which is configured to provide both the first image information $I_1$ and the second image information $I_2$.

According to an exemplary embodiment of the present invention, as shown and described for example later on with respect to FIG. 4, the camera arrangement 10 may comprise a first camera device 10-1, which is configured to provide the first image information $I_1$, and a second camera device 10-2, which is configured to provide the second image information $I_2$. The first camera device 10-1 is configured to record the first image information $I_1$ in a first position, and the second camera device 10-2 is configured to record the second image information $I_2$ in a second position.

The first and/or second wavelength bands for camera arrangement 10 may be in the visible or non-visible light spectrum comprising several wavelength bands as for instance:
(1) Blue: 0.450-0.520 µm (micrometer)
(2) Green: 0.515-0.600 µm
(3) Red: 0.60-0.69 µm
(4) Visible: 0.45-0.7 µm
(5) Infrared: 0.7-1.0 µm
(6) Near infrared: 1.0-3.0 µm
(7) Mid infrared: 3.0-50.0 µm
(8) Far infrared: 50.0-1000.0 µm In the non-visible light spectrum, blood vessels may be better optically resolvable, i.e. a contrast above a predefined threshold value, which allows tracking the position markers more accurately.

According to an exemplary embodiment of the present invention, by triangulation and using two different camera positions, the generation of a three-dimensional model of structures or a three-dimensional model of the whole patient may be improved.

According to an exemplary embodiment of the present invention, the data processor device 30 may be configured to generate the fused image IE based on the first image information $I_1$ and the second image information $I_2$ using the three-dimensional model of structures identified by the detected landmarks M in the fused image IE.

Detecting and spectrally resolving the landmarks M used as position markers allows a three-dimensional positioning of structures, which are related to the position markers M. In other words, each of the position markers is assigned to a certain structure part allowing tracking the motion, if time-dependent image series are recorded, or allowing to position the assigned structure within the three-dimensional space.

According to an exemplary embodiment of the present invention, the camera devices 10-0, 10-1, 10-2 may be a hyperspectral or multispectral filter-wheel camera for hyperspectral or multispectral imaging with a spectral range of 400 to 1000 nm (nanometer) or from 1000 to 1700 nm or from 500 to 1700 nm, with various, for instance 6 or 8 or even more interchangeable filters, with a charge-coupled device CCD with a resolution of 1392×1040 pixels or physical points in a raster image, or, for instance with an Indium gallium arsenide (InGaAs) or any other semiconductor sensor with a resolution of 640×512 pixels, or with a sensor with any other pixel resolution.

The term "hyperspectral imaging" as used by the present invention refers to collecting and processing information from across a range of the electromagnetic spectrum extending beyond the visible range.

The term "multispectral imaging" as used by the present invention refers to capturing image data at specific frequencies across the electromagnetic spectrum. The wavelengths may be separated by filters or by the use of instruments that are sensitive to particular wavelengths, i.e. multiple spectra are used, which is the reason for the term "multispectral imaging". This may include light from frequencies beyond the visible light range, such as infrared, which then may also be defined by the term "hyper" of the aforementioned term "hyperspectral imaging".

Spectral—be it multispectral or hyperspectral—imaging may allow extraction of additional information from an image, especially information that the human eye fails to capture with its receptors for red, green and blue.

According to an exemplary embodiment of the present invention, the camera arrangement 10 may have a frame rate of 10 fps (frames per second) or 16 fps or 20 fps or any other, for instance faster frame rate.

According to an exemplary embodiment of the present invention, the imaging system 100 may further comprise an X-ray device 40. The X-ray device 40 may be used to record X-ray image information $I_3$ in form of X-ray images of the patient P. The X-ray image information $I_3$ may be further used when generating the fused image IE or when generating the three-dimensional model of structures.

According to an exemplary embodiment of the present invention, the imaging system 100 may further comprise a display device 50 configured to display the fused image IE.

Figure 2:
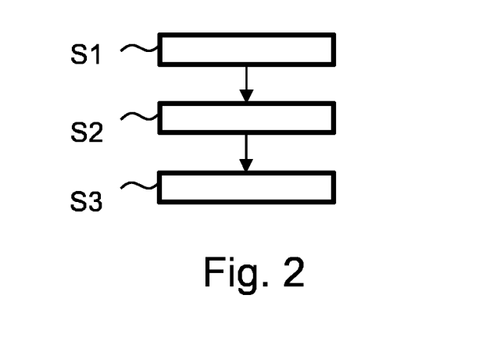
FIG. 2 shows a schematic flowchart diagram of a method for generating an image of a patient according to an exemplary embodiment of the present invention.

FIG. 2 shows a schematic flow-chart diagram of a method for generating an image of a patient according to an exemplary embodiment of the present invention. The method for generating an image of the patient may comprise the following steps:

As a first step of the method, providing S1 a first image information $I_1$ of the patient P using a first wavelength band by a camera arrangement 10 is performed.

As a second step of the method, providing S2 a second image information $I_2$ of the patient P using a second wavelength band by the camera arrangement 10 is performed; wherein the first wavelength band and the second wavelength band are different; and wherein the first and/or second image information comprises landmark information of landmarks M of a patient P, wherein the landmark information is derived by at least one wavelength band outside the visible spectrum.

As a third step of the method, generating S3 a fused image IE based on the first image information $I_1$ and the second image information $I_2$ by a data processor 30 and detecting the landmarks M in the fused image IE is performed.

Figure 3:
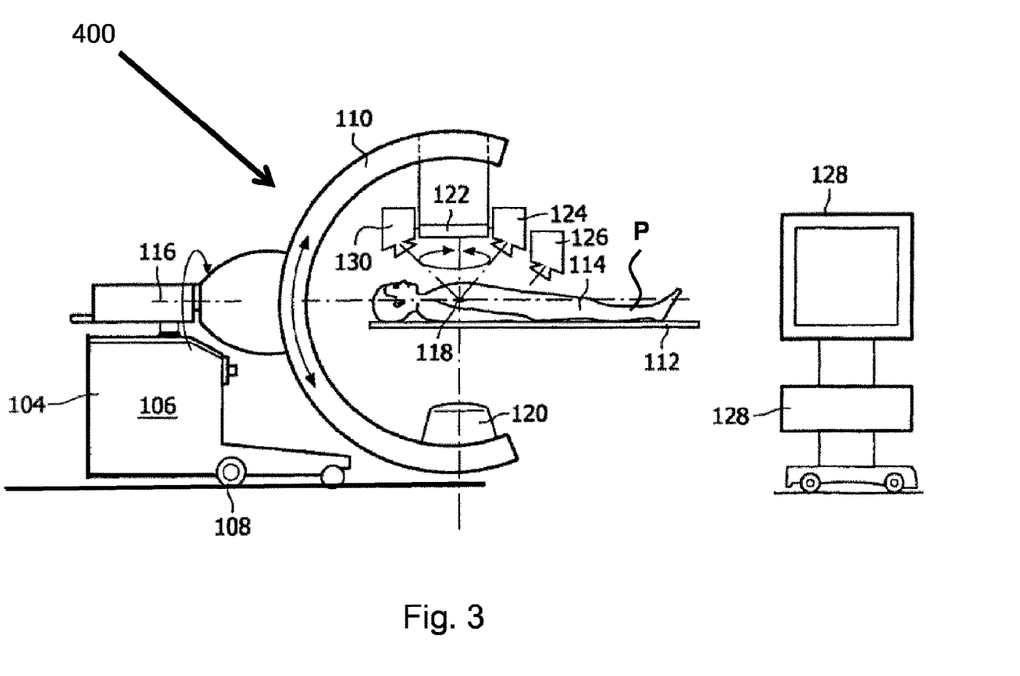
FIG. 3 shows a schematic diagram of a medical imaging system according to an exemplary embodiment of the present invention.

FIG. 3 schematically shows a medical imaging device 400 comprising an X-ray device 104 for providing an X-ray image of a patient's interior according to an exemplary embodiment of the present invention. The X-ray device 104, see FIG. 3, has a base frame 106 supported by wheels 108, a movable C-arm 110 and a surgical table 112 for supporting a patient 114, also referred to with the reference P, which patient 114 is a human being in this particular example.

The C-arm 110 is rotatable with regard to a primary axis 116, which primary axis 116 has a direction corresponding to a main orientation of the surgical table 112, and to a secondary axis 118, which secondary axis 118 is perpendicular to the primary axis 116 and parallel to the surgical table 112. An X-ray source 120 and an X-ray detector 122, which is preferably a rectangular and flat detector, are mounted on the C-arm 110 such that the X-ray source and the X-ray detector reside opposite one another with respect to the secondary axis 118.

A first camera 124, which is provided as the first camera device 10-1 for providing a stream of camera images of a patient's exterior, is mounted on the C-arm 110 aside the X-ray detector 122. In this specific example, the first camera 124 may be sensitive to wavelengths in the visible spectrum. The first camera 124 may also be provided to capture a stream of images or single images at different time points.

A second camera 126, which is provided as the second camera device 10-2 for providing a stream of camera images of a patient's exterior, is mounted on the C-arm 110 aside the X-ray detector 122. In this specific example, the second camera 126 may be sensitive to wavelengths in the visible spectrum. The second camera 126 may also be provided to capture a stream of images or single images at different time points.

Referring to FIG. 3, a data processor 128, 30 renders the X-ray image and the stream of camera images into a stream of composite images based on the spatial correlating provided by the movable marker. The stream of composite images displays the patient's interior and the patient's exterior in a geometrically overlapping sense, and furthermore the moveable marker, the surgical field, the tumor and the patient's body contour.

Figure 4:
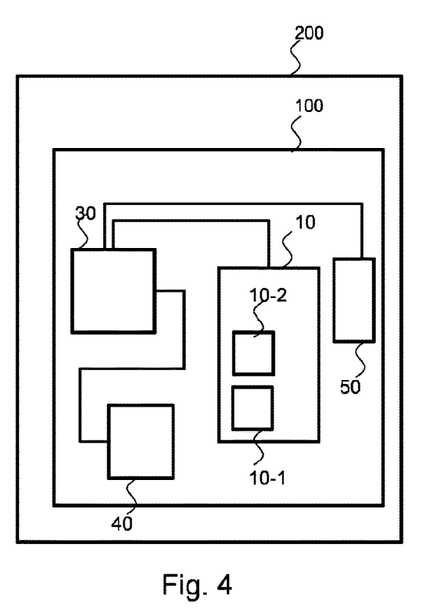
FIG. 4 shows a schematic diagram of a medical imaging system according to an exemplary embodiment of the present invention.

FIG. 4 shows a schematic diagram of a medical imaging system 200 according to a further exemplary embodiment of the present invention.

The medical imaging system 200 may comprise an example of the imaging device 100, an example of the display device 50, and an example of the X-ray device 40. The display device 50 may be configured to display the fused image IE. The X-ray device 40 may be configured to provide X-ray image information $I_3$ of the patient P. The data processor 30 may be configured to generate the fused image IE based on the first image information $I_1$ and the second image information $I_2$ and the X-ray image information $I_3$. The camera arrangement 10 may comprise the first camera device 10-1, which is configured to provide the first image information $I_1$, and the second camera device 10-2, which is configured to provide the second image information $I_2$.

According to an exemplary embodiment of the present invention, the imaging system 200 may provide the option to use blood vessels as natural markers by combining optical cameras with hyperspectral cameras. Preferably, the wavelength bands of the multi- or hyperspectral cameras contain one band in the visible range and one band in the invisible range. A fused image may be created from the two images from each band, which shows the blood vessels in high contrast. The image fusion may include, for instance, a partial subtraction.

Figure 5:
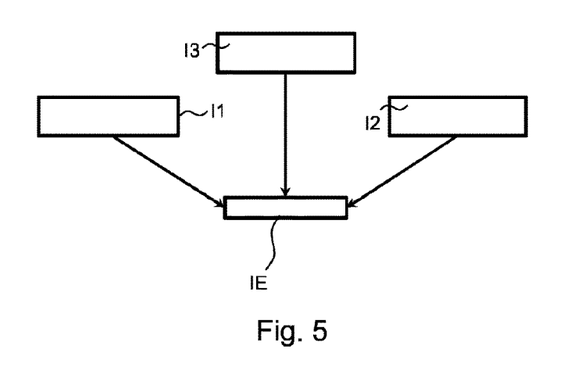
FIG. 5 shows a schematic diagram of the process of generating a fused image for explaining the present invention.

FIG. 5 shows a schematic diagram of the process of generating a fused image for further explaining the present invention.

The fused image IE may be based on merging the first image information $I_1$ and the second image information $I_2$ using a three-dimensional model of structures identified, e.g. blood vessels or other superficial tissue structure in the skin. The resolved landmarks M may serve as position markers for further processing as performed by the data processor 30.

As a further basis for generating the fused image IE, also the X-ray image information $I_3$ may be used by the data processor 30.

Figure 6:
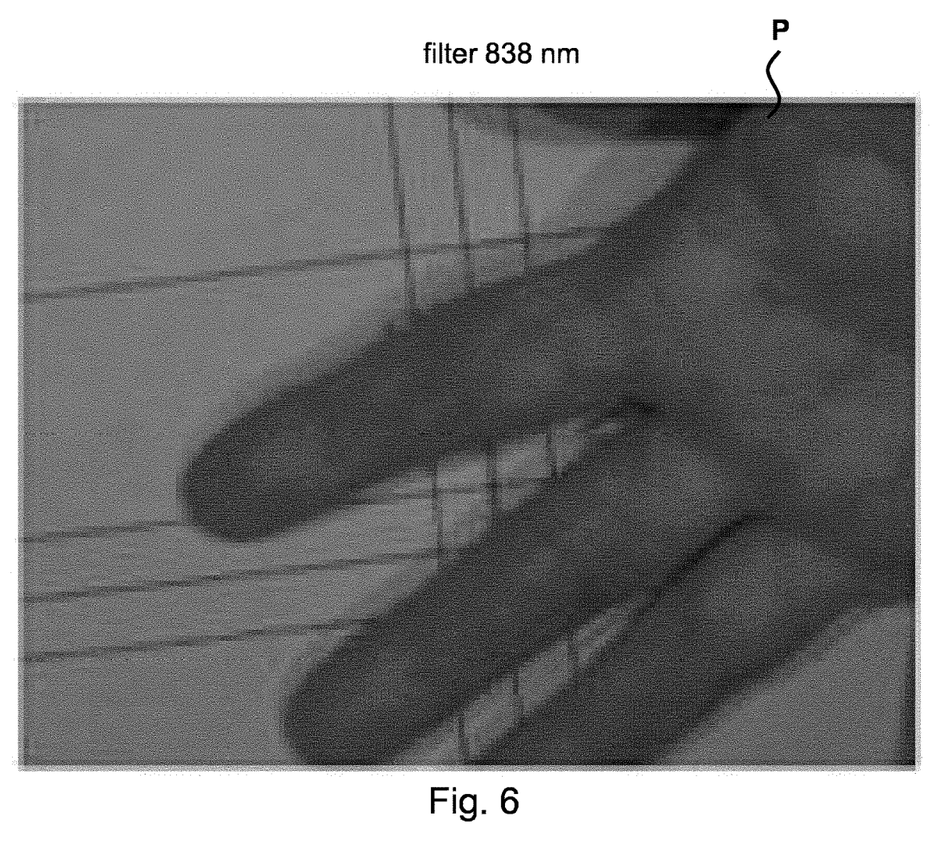
FIG. 6 shows a schematic diagram of an image recorded by a camera device for explaining the present invention.

FIG. 6 shows a further image for explaining the present invention.

The image may be recorded, for instance, by the first camera device 10-1. The image may capture a hand of the patient P. For recording the image, a filter of 838 nm with a bandwidth of 10 nm may be used.

Figure 7:
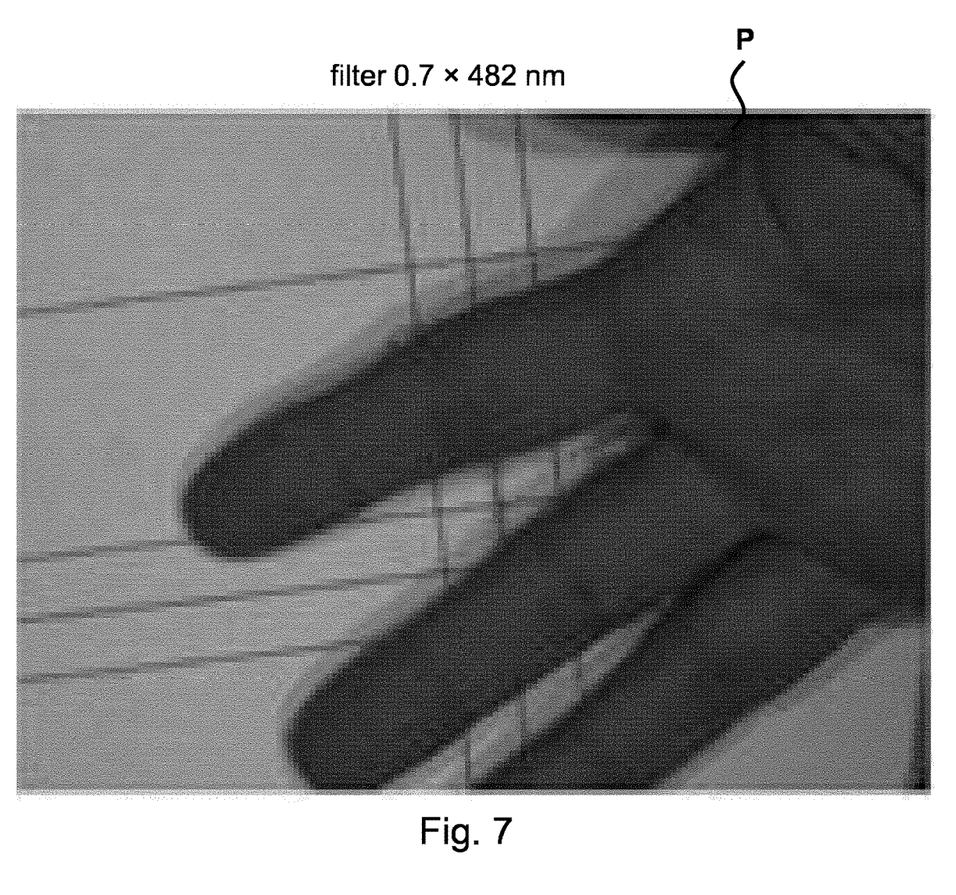
FIG. 7 shows an image recorded by a second camera device for explaining the present invention.

FIG. 7 shows an image of the hand of the patient P, taken at a filter of 482 nm where the filter has a bandwidth of 10 nm, recorded, for instance, by the second camera device 10-2. The factor 0.7 indicates that the filter attenuates the intensity by a factor of 0.7.

Alternatively, instead of two camera devices, a single multi-spectral camera device 10-0 may be used. During imaging, for example, filters of 838 nm and 482 nm may be employed in an alternating manner.

Figure 8:
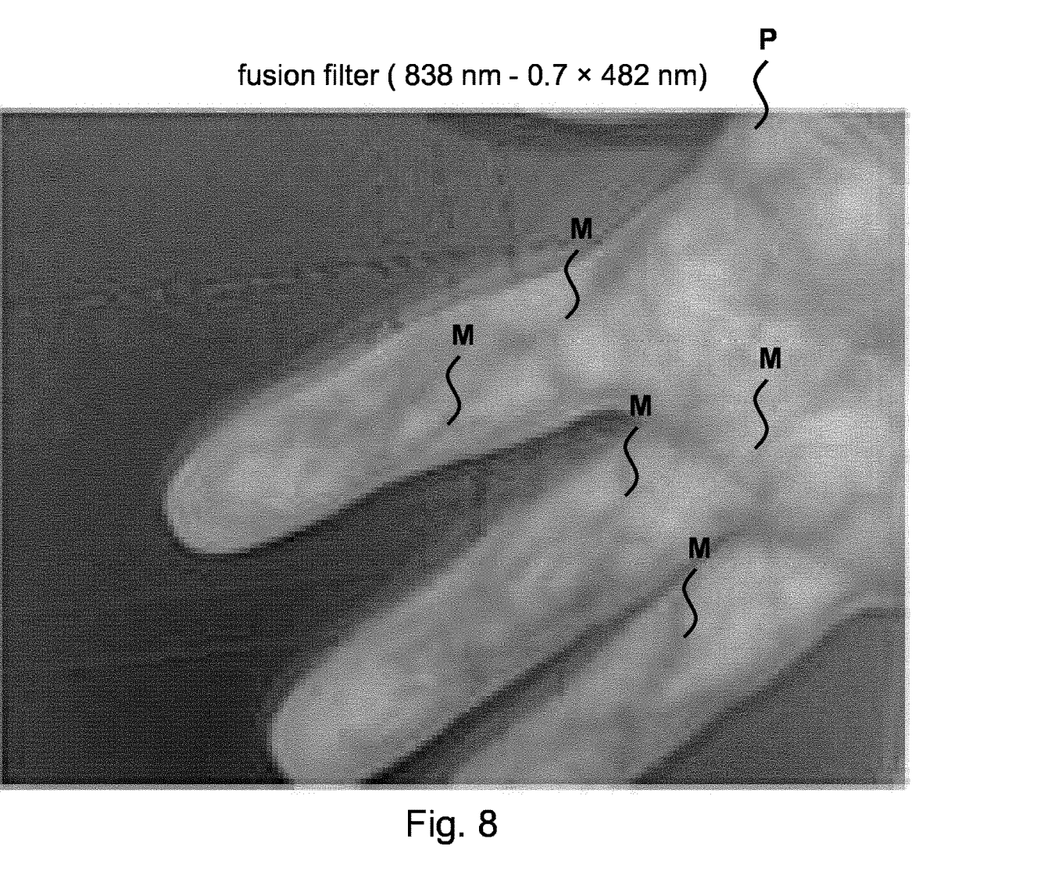
FIG. 8 shows an image as generated by a medical imaging system according to an exemplary embodiment of the present invention.

FIG. 8 shows an image using a fusion filter, which is a combination of the images as depicted in FIGS. 6 and 7. The combination as shown in the image of FIG. 8 may be, for instance, a partially subtraction or any other type of calculation performed in connection with the two images as depicted in FIGS. 6 and 7.

In a further embodiment, a multi-spectral camera performing imaging at more than two wavelengths may be employed. For example, a third filter passing light at a wavelength around 680 nm may be added. In this embodiment, for example, the fused image is based on a weighted combination of the images acquired in the different wavelength bands. The weighting is preferably tuned so as to bring out the natural markers of interest at a contrast level sufficient for image tracking in accordance with the invention.

It has to be noted that embodiments of the present invention are described with reference to different subject-matters. In particular, some embodiments are described with reference to method type claims whereas other embodiments are described with reference to device type claims.

However, a person skilled in the art will gather from the above and the foregoing description that, unless otherwise notified, in addition to any combination of features belonging to one type of subject-matter also any combination between features relating to different subject-matters is considered to be disclosed within this application. However, all features can be combined providing synergetic effects that are more than the simple summation of the features.

While the present invention has been illustrated and described in detail in the drawings and the foregoing description, such illustration and description are to be considered illustrative or exemplary and not restrictive; the present invention is not limited to the disclosed embodiments.

Other variations to the disclosed embodiments can be understood and effected by those skilled in the art and practicing the claimed invention, from a study of the drawings, the disclosure, and the appended claims.

In the claims, the word "comprising" does not exclude other elements or steps, and the indefinite article "a" or "an" does not exclude a plurality. A single processor or controller or other unit may fulfill the functions of several items recited in the claims.

The mere fact that certain measures are recited in mutually different dependent claims does not indicate that a combination of these measures cannot be used to advantage. Any reference signs in the claims should not be construed as limiting the scope.

The invention claimed is:

1. An imaging device for generating an image of a patient, the imaging device comprising:
    a camera configured to provide first image information of the patient using a wavelength band within the infrared spectrum as a first wavelength band and second image information of the patient using a wavelength band within the visible spectrum as a second wavelength band, wherein one or more of the first and second image information comprises landmark information of blood vessels or other superficial tissue structures in the skin of a patient as natural markers; and
    processing circuitry configured to generate a fused image by applying a fusion filter to combine the first image information with the second image information to generate the fused image, wherein the processing circuitry is configured to detect the natural makers in the fused image and display the natural markers in a contrast above a predefined threshold value.

2. The imaging device according to claim 1, wherein the camera is configured to record the first image information in a first position with respect to the patient, and to record the second image information in a second position with respect to the patient.

3. The imaging device according to claim 1, wherein the camera is configured to provide both the first image information and the second image information.

4. The imaging device according to claim 2, wherein the camera comprises a first camera configured to provide the first image information, and a second camera configured to provide the second image information; and
    wherein the first camera is configured to record the first image information in the first position, and the second camera is configured to record the second image information in the second position.

5. The imaging device according to claim 4, wherein the first camera, for recording the first image information, employs a bandpass filter of 838nm with a bandwidth of 10nm.

6. The imaging device according to claim 4, wherein the second camera, for recording the second image information, employs a bandpass filter of 482nm with a bandwidth of 10nm.

7. The imaging device according to claim 1, wherein the processing circuitry is configured to generate a three-dimensional model of structures from the natural markers.

8. The imaging device according to claim 1, further comprising a display for displaying the fused image.

9. The imaging device according to claim 1, wherein the processing circuitry is configured to detect a motion of the patient based on a continuous recording by the camera and to continuously generate the fused image, resulting in a fused video data steam.

10. A medical imaging system comprising:
    an imaging device according to claim 1;
    a display for displaying the fused image; and
    an X-ray for providing X-ray image information of the patient;
    wherein the processing circuitry is configured to generate the fused image based on the first image information, the second image information, and the X-ray image information.

11. A method for generating an image of a patient, the method comprising:
    providing a first image information of the patient using a first wavelength band by a camera;
    providing a second image information of the patient using a second wavelength band by the camera, wherein the first wavelength band and the second wavelength band are different, and wherein one or more of the first and second image information comprises landmark information of blood vessels or other superficial tissue structures in the skin of a patient as natural markers;
    generating a fused image by applying, via processing circuitry, a fusion filter to combine the first image information with the second image information to generate the fused image such that the fused image displays the natural markers in a contrast above a predefined threshold value based on the first image information and the second image information; and
    detecting the natural markers in the fused image.

12. A non-transitory computer-readable medium having stored thereon a computer program including instructions for controlling an apparatus which, when being executed by processing circuitry, is configured to:
    provide a first image information of the patient using a first wavelength band by a camera;
    provide a second image information of the patient using a second wavelength band by the camera, wherein the first wavelength band and the second wavelength band are different, and wherein one or more of the first and second image information comprises landmark information of blood vessels or other superficial tissue structures in the skin of a patient as natural markers;
    generate a fused image by applying a fusion filter to combine the first image information with the second image information to generate the fused image such that the fused image displays the natural markers in a contrast above a predefined threshold value based on the first image information and the second image information; and
    detect the natural markers in the fused image.

13. The imaging device according to claim 1, wherein the processing circuitry is configured to detect corresponding position markers in each of the first image information and second image information and to generate the fused image based on the detected corresponding position markers.

14. The imaging device according to claim 1, wherein the fusion filter comprises a partial subtraction of the first image information from the second image information.

15. The method according to claim 11, comprising detecting corresponding position markers in each of the first image information and second image information and generating the fused image based on the detected corresponding position markers.

16. The method according to claim 11, wherein applying the fusion filter comprises applying a partial subtraction of the first image information from the second image information.

17. The non-transitory computer readable medium of claim 12, comprising instructions, that when executed by processing circuity is configured to cause the processing circuitry to detect corresponding position markers in each of the first image information and second image information and generate the fused image based on the detected corresponding position markers.

18. The non-transitory computer readable medium of claim 12, comprising instructions, that when executed by processing circuity is configured to cause the processing circuitry to apply a partial subtraction of the first image information from the second image information.

\* \* \* \* \*